Dec. 3, 1929. E. I. McKESSON Re. 17,512

RESPIRATOR

Original Filed March 17, 1913 4 Sheets-Sheet 1

Elmer I. McKesson
INVENTOR
BY
ATTORNEY

Dec. 3, 1929. E. I. McKESSON Re. 17,512
RESPIRATOR
Original Filed March 17, 1913 4 Sheets-Sheet 2
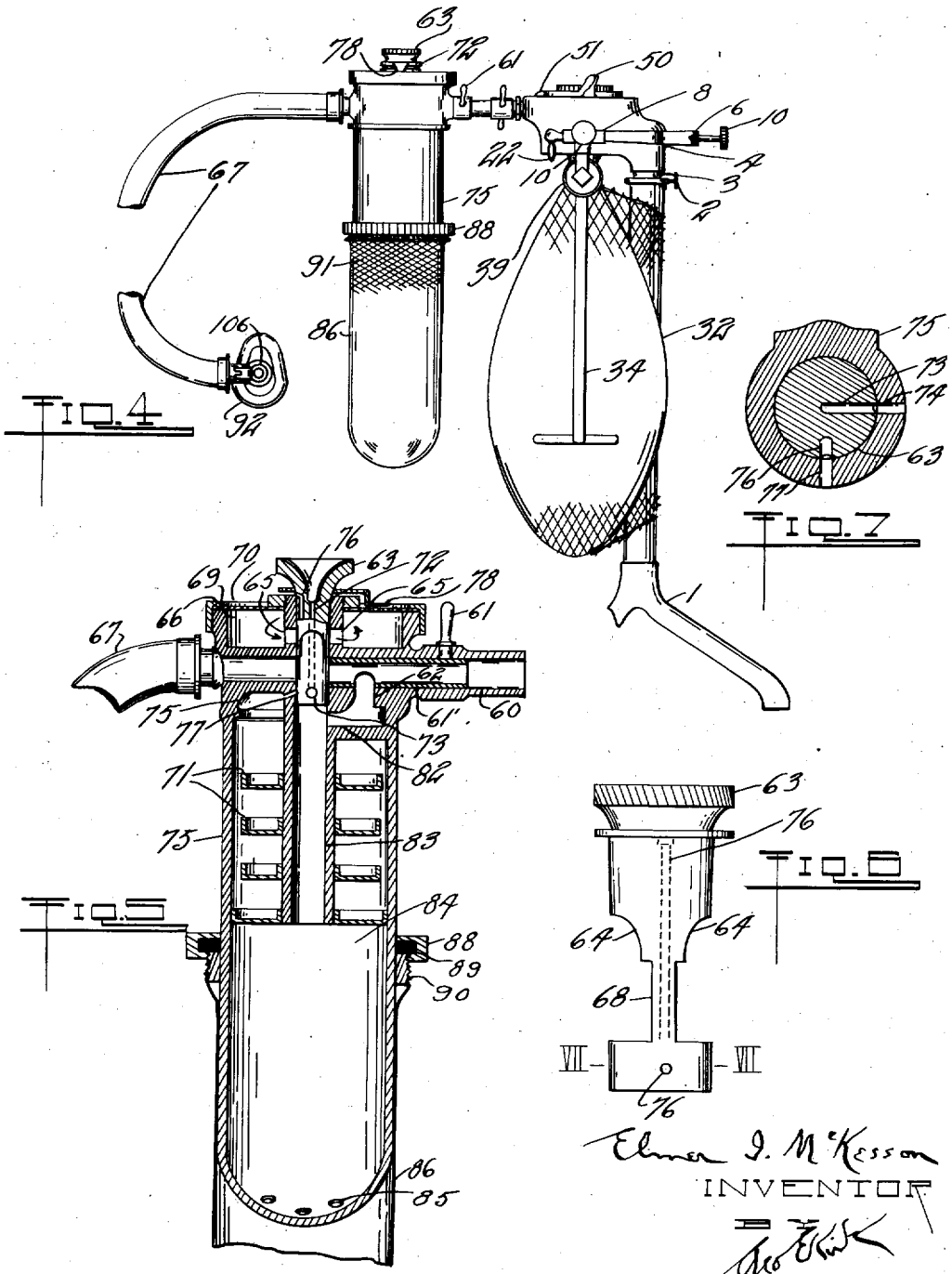
Elmer I. McKesson
INVENTOR
BY
Geo. Kirk
ATTORNEY Dec. 3, 1929. E. I. McKESSON Re. 17,512
RESPIRATOR
Original Filed March 17, 1913 4 Sheets-Sheet 3
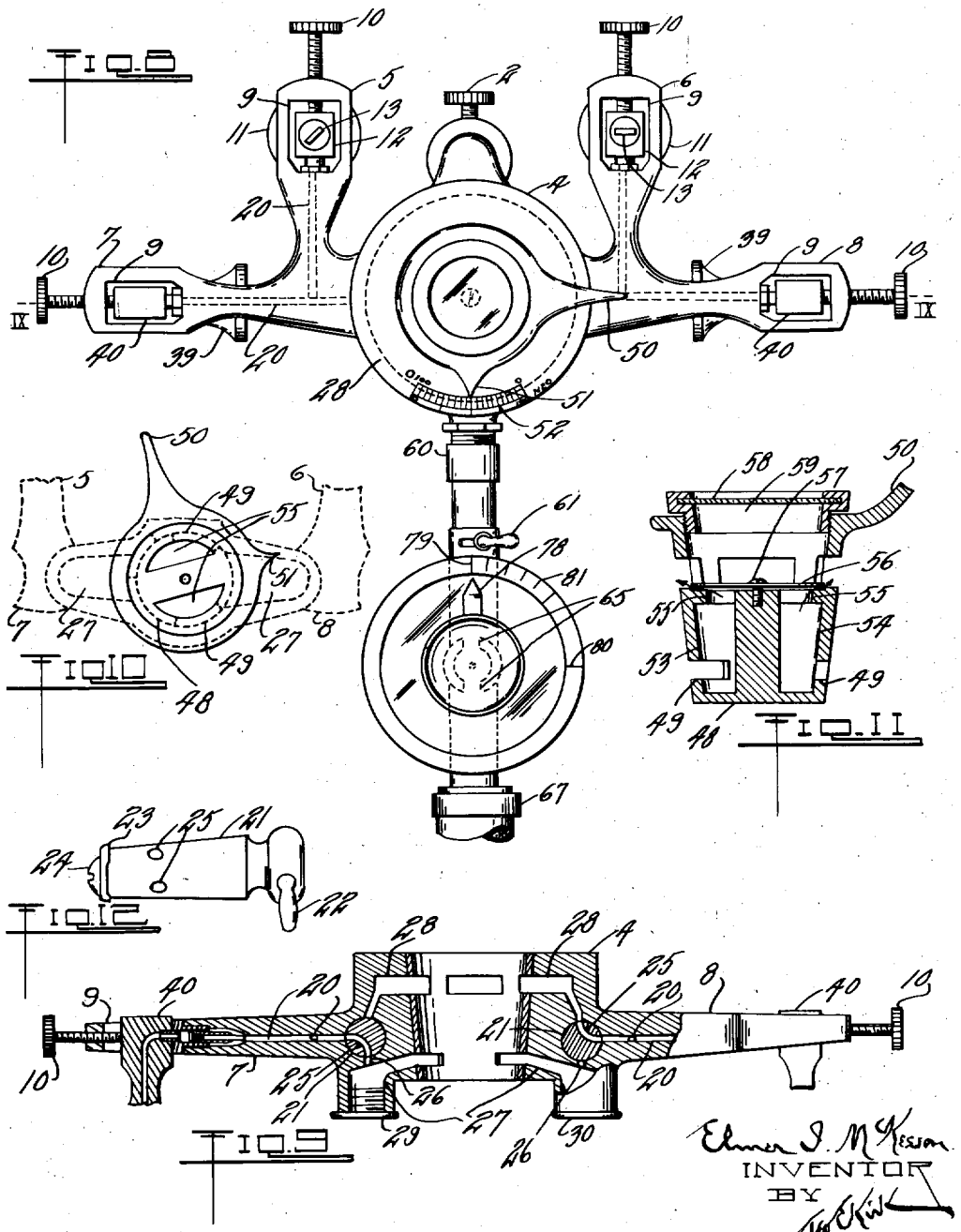
Elmer I. McKesson
INVENTOR
BY
Geo. E. Kirk
ATTORNEY Dec. 3, 1929. E. I. McKESSON Re. 17,512
RESPIRATOR
Original Filed March 17, 1913 4 Sheets-Sheet 4
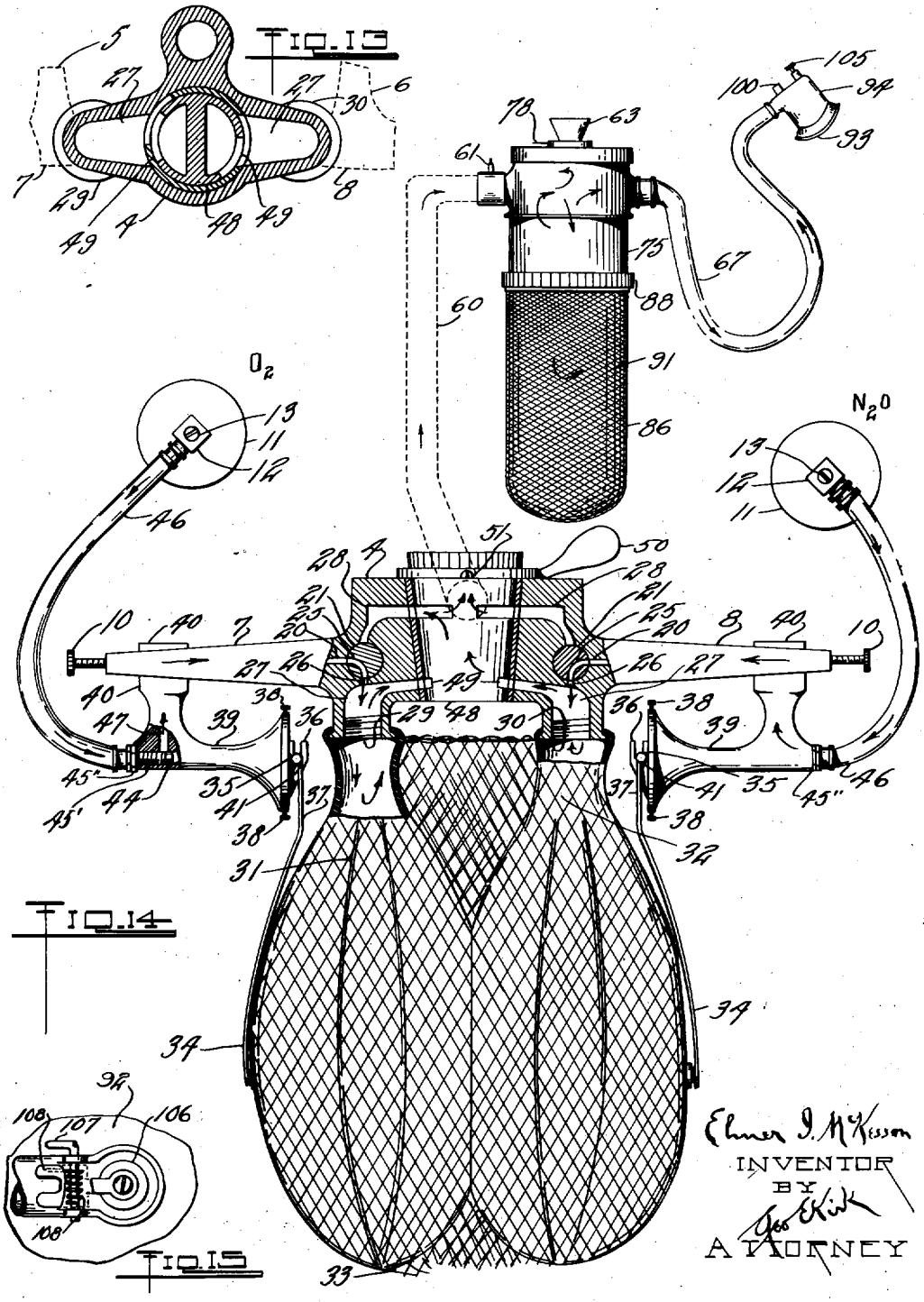

Reissued Dec. 3, 1929 Re. 17,512

UNITED STATES PATENT OFFICE

ELMER I. McKESSON, OF TOLEDO, OHIO

RESPIRATOR

Original No. 1,320,900, dated November 4, 1919, Serial No. 754,682, filed March 17, 1913. Application for reissue filed August 13, 1924. Serial No. 731,880.

This invention relates to the control and mixing of fluids and vapors and their conduct for various uses in breathing.

This invention has utility when embodied in mechanisms for analgesia, anesthesia, and resuscitation, having wide range of utility in dental, general surgical work, as well as in cases of asphyxiation.

Referring to the drawings:

Fig. 4 is a fragmentary side elevation of the respirator with a face nozzle adapted thereto;

Fig. 5 is a fragmentary sectional view of a vaporizer and rebreathing reservoir;

Fig. 6 is an enlarged detail view in side elevation of the vaporizer control and filling member or valve;

Fig. 7 is a section on the line VII—VII, Fig. 6, showing in addition the ports with which the filling valve coacts;

Fig. 8 is a plan view of the respirator;

Fig. 9 is a fragmentary section on the line IX—IX, Fig. 8, looking in the direction of the arrow;

Fig. 10 is a plan view of the proportioning valve with the check plate and sight removed turned to off position;

Fig. 11 is a medial longitudinal section of the proportioning valve;

Fig. 12 is a detail view in side elevation of a cut off or by-passing valve;

Fig. 13 is a fragmentary detail view of the casing with the proportioning valve therein; and Fig. 14 is a general view, partially in section, diagrammatic as to assembly, of the apparatus; and Fig. 15 is a fragmentary detail view of the face inhaler adjustable relief or exhaling valve.

Figure 1:
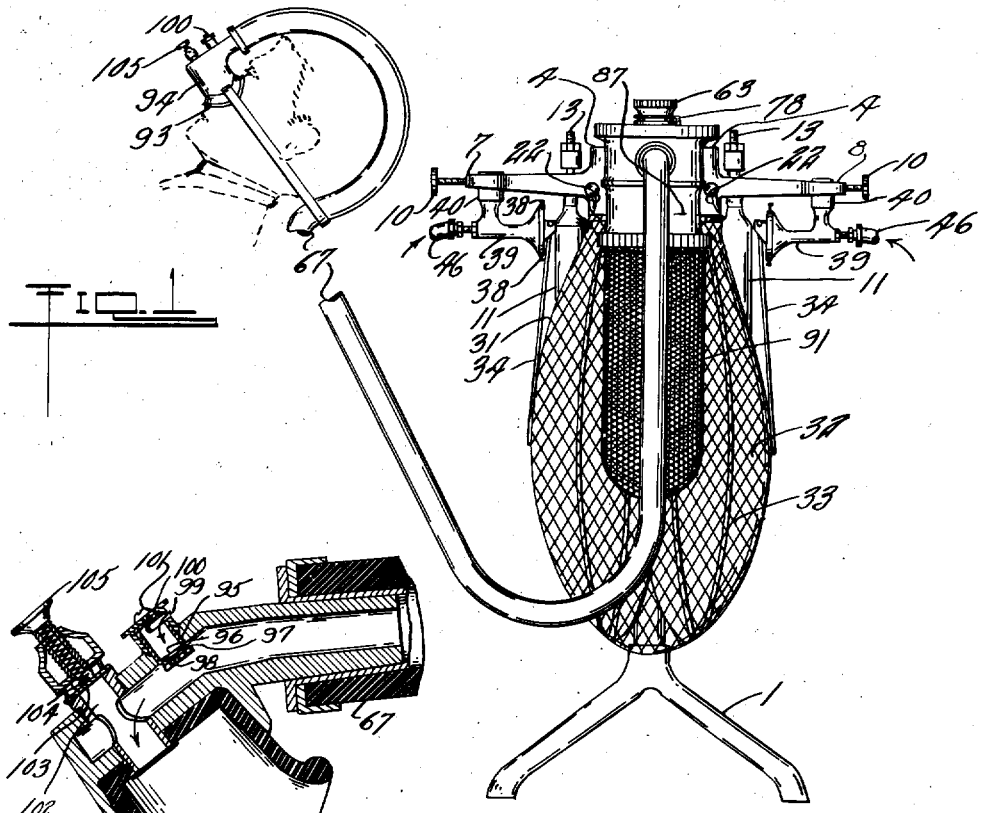
Fig. 1 is an elevation of an embodiment of the invention adapted for analgesia and anesthesia, as in dental work.

The respirator is provided with the standard 1 or mounting (Fig. 4) having the set screw 2 adjustable to lock the stem 3 in various telescoped positions for carrying the main frame 4. This main frame 4 is provided with fluid supply reservoir carrying arms 5, 6, and additional similar arms 7, 8, shown as adapted to carry fluid supply reservoirs, or reserve fluid supply automatic replenishing means. These arms 5, 6, 7, 8, (Fig. 8) are provided with head receiving recesses 9 and set screws 10 to engage heads disposed in such recesses.

When the respirator is used as a portable apparatus, and say especially when used for surgical and resuscitation work, or when it is desired to have assured at all times an emergency supply of nitrous oxid and oxygen, or such fluids as may be used, the compressed fluid drums, containers, or reservoirs 11 having heads 12 provided with controlling valves 13, may be locked by the set screws 10 in the respective heads 5, 6.

Figure 3:
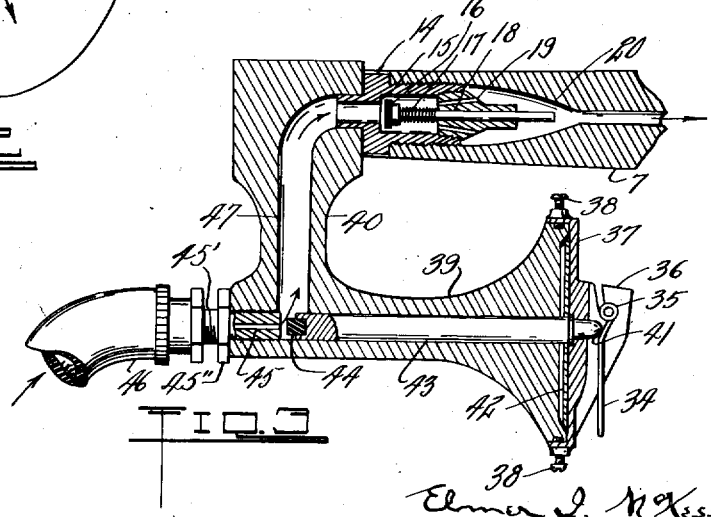
Fig. 3 is a sectional view, on an enlarged scale, of a reserve supply replenishing means control.

Each of these arms 5, 6, 7, 8, is provided with a bushing 14 (Fig. 3) having a central duct 15 therethrough providing in its extent a seat for the plunger 16 normally held against said seat by the spring 17. The travel of the plunger 16 is guided by the stem 18 connected thereto, which stem is reciprocable in the bushing 14. The spring 17 is mounted about this stem 18. Adjacent the stem 18 and through the portion of the bushing 14 serving as the stem guide are openings 19 in communication with the duct 20 (Figs. 3, 9). This mechanism is a check valve for each arm allowing delivery of fluid under pressure into the reserve fluid supply ducts 20 but effectually serving to prevent escape of fluid through the arms 5, 6, 7, 8, at the recesses 9, should the pressure run low in the supply reservoir, or the supply be disconnected.

These ducts 20 lead to the cut off or by-pass valves 21, (Figs. 1, 9, 12, 14.) These valves 21 are provided with handles 22. To maintain the stems 21 snugly seated, the spring clips 23 are set up by the screws 24. The curved passage 25 in the valve 21 may register with the duct 20 and the duct 26 in communication with the passage 27. This valve may have a second connecting position by having its passage 25 connect the duct 20 with the passage 28, while at other positions it may effectively cut off duct 20.

The passages 27 terminate in lipped or shouldered openings 29, 30, upon which are mounted the flexible reservoirs or fluid tight rubber bags 31, 32, enveloped by the single or common covering or mesh 33. This net 33 serving as an envelop for the two reservoirs, effectively equalizes the pressure of the fluid in the two reservoirs, by limiting the distension of the bags 31, 32, as adjusted or determined in the tightening into which draw string 33′ is tied.

The fluid in the expansion members or reservoirs 31, 32, (Figs. 1, 8) may be replenished from the tanks 11, intermittently by adjusting the valves 13, or in continued use by delicately adjusting the valves 13. Such operation requires careful supervision. To avoid the concern and care of such manipulation, automatic replenishing mechanism may be used (Figs. 1, 3, 4, 14). Lever arms 34 are given a desired or adjusted bend and so disposed as to coact with the bags or reservoirs 31, 32, to be actuated by the distension thereof, said levers having their fulcra or pivot mountings 35 removably carried in the hook brackets 36 of the rigid disks 37 mounted by the set screws 38 on the arms 39 of the heads 40. The disk 37 is a guide for the plunger 41 most delicately controlled by the lever 34. These plungers 41 seat against the air tight diaphragms 42, and any distension of the reservoirs 31, 32, rocks the levers 34, and at the determined adjusted pressures are effective to push the plungers 41 against the diaphragms 42, causing the plungers 43 in the arms 39 to move their seats 44 to close the port 45 from the reserve supply duct or passage-way 46, in communication with a source of fluid supply under pressure, (Fig. 14) thereby shutting off the supply of fluid to the passage 47 through the head 40, ducts 15, 20, 25, 26, 27, to the replenished reservoir 31 or 32. When the direct fluid supply in the reservoir 31, or 32, again falls so that the lever 34 may move a little in taking up such decrease in distension, seat 44 is opened to permit automatically a replenishment of supply from any reserve source to which the duct 46 may be connected. Port 45 through externally threaded duct sections 45′ is so adjusted toward the seat 44 as to coact with the seat 44 of the plunger 43 when the lever 34 hangs for the desired capacity of the bag 31, or 32. This adjustment of the sections 45′ is under the control of the operator and is normally to approximate similar size for the bags 31, 32. Each size adjustment, due to the lever control, changes the pressure. When adjusted the sections are so held against disturbance by nuts 45″, which are readily slacked off for a change of adjustment and thus a change in pressure. The seat 44 is adjusted for such distension or presure in bags 31, 32 as may be desired. Under the higher pressures in the bags, the gases are held from wastage only by increasing the tension of spring 104 by tightening screw 105 (Fig. 2) on the face or nasal inhalers. The levers 34 are of pliable metal and are bent to conform to the shape of the bags 31, 32, and in further adjusting their size and pressure. There is accordingly insured uniform direct fluid supply for even most extended operations without need of any attention whatever upon the part of the user of the respirator.

There is economy in the use of fluid supplied with each inhalation but checking stopping the flow of fluids during intervals or portions of intervals of each exhalation when such flow of fluids has replenished the direct supply and might escape and be wasted. The stopping of the flow of fluids into bags 31 and 32, when the desired pressure is secured in these containers, serves to increase the safety for the patient by equalizing and assisting in maintaining constant proportions at different rates of consumption as affected by the greatly variable rates of respiration in patients. The supply of the fluid is at a uniform pressure, and there is safety for the patient, due to this automatic replenishing means.

Figure 2:
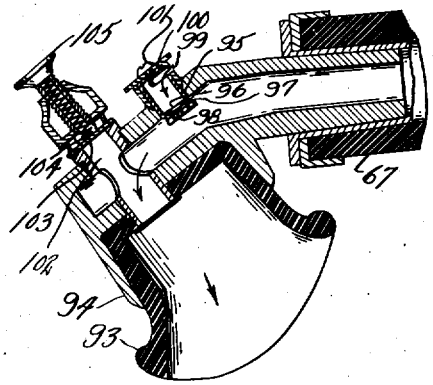
Fig. 2 is a sectional view, on an enlarged scale, of a nasal nozzle for the respirator.

The frame 4 carries the proportioning valve (Figs. 9, 10, 11, 14). The proportioning valve 48 has the ports 49 coacting with the direct fluid supply passages 27 in communication with the reservoirs 31, 32. By moving the handle 50 of the valve 48, the definite proportions of the fluid to be mixed may be shown by the pointer 51 traveling along the percentage scales 52. The scales are indicated as for nitrous oxid and oxygen with the pointer 51 (Fig. 8) at 50% of each. The graduations are 5%. The indicated proportions are real, as thus predetermined, in this proportioning valve mechanism as the gases from the respective passage-ways enter the mixing chamber, for the envelop 33 keeps the pressure of the direct fluid supply reservoirs 31, 32, the same. For each adjustment of the pressure in the reservoirs 31, 32, there is a definite rate of flow to the mixing chamber 59. If this change be one of increase in pressure, it increases the facility of machine response to the demands of the patient. In thus keeping the pressures equal, the mesh bag 33 is a means simultaneously coacting with the two bags 31, 32, determining the relative pressures as equal, and with such pressures equal that the proportions as adjusted are maintained. In the manipulation of the proportioning valve 48, either reservoir 31, or 32, may be completely cut off, as well as both. For this latter condition the handle 50 is thrust counterclockwise 90°, or slightly more, away from the 50% nitrous oxid 50% oxygen position of Figs. 8, 13. This shifts the pointer 51 past the 100% nitrous oxid into approximate alignment with the arm 8 (Figs. 1, 2, 3). Accordingly, by operation of this single shiftable valve handle 50, either nitrous oxid alone, or oxygen alone, may be delivered to the inhaler or shut off from said inhaler 92 or 93.

To preclude back pressure permitting any intermingling of the supplies in the reservoirs 31, 32, the chambers 53, 54, to which the ports 49 connect, have their common plane outlet ports 55 closed by the check valve or disk plate member 56, the travel limit of which in opening may be adjusted by the set screw 57, as an indicating means permitting the operator to observe whether fluid supply is being taken by the patient, the sight 58 may be provided in closing the mixing chamber 59 above the member 56, so that any movements of this member 56 may be plainly seen, serving as a sure indication that the patient breathes sufficiently deep to obtain fresh or unused fluids from containers 31 and 32. This member 56 is a single element simultaneously closing both supplies against back pressure, but lifting on unbalanced pressure either from the reservoirs 31, 32, or inhalation. The proportioning valve 48 is a single element simultaneously adjusting the relative quantities of the supplies. Considerable utility in practice results from this simple compact structure so susceptible of delicate regulation. This valve 48 has tapered friction seating engagement in the frame 4.

The chamber 59 is in communication with the passages 28 (Figs. 8, 9, 14) leading to the delivery duct 60 in or upon which may be mounted the vaporizing and rebreathing reservoir, herein shown as a combined structure (Fig. 5). To by-pass the rebreathing reservoir the handle 61 may be manipulated to cause the sleeve 61′ to close the port 62. With the vaporizer inactive the valve member 63 has its ports 64 out of registry with the ports 65, thus there is direct connection of the delivery duct 60 with the duct 67 leading to the patient. Manipulation of the single shiftable valve 61′ by the handle 61 closes the port 62, the gas or mixed gases from the mixing chamber 59 pass to the inhaler alone, while with this port 62 open, such gas or mixed gases pass both to the inhaler and to this gas bag 86.

In the use of the vaporizer, say for ether or chloroform, or such substance as occasion may demand, the sleeve 61′ may close the port 62 to cut out the rebreathing reservoir, or be open to permit the use of the rebreathing reservoir. The fluid to be laden with vapor from the vaporizer, enters by way of the delivery duct 60, and with the member 63 rotated so that its central section 68 closes the straight passage of the duct 60, the ports 64 are in registry with the ports 65 and the fluid is thus caused to pass through the chamber 69 as indicated by the arrows (Fig. 5). The chamber 69 is closed by the sight plate or glass cover 70. The lower portion of the chamber 69 contains pans or shelves 71 over which the liquid supplying the vapor may be distributed, the overflowing of which pans 71 provides a maximum of evaporative area. In charging the vaporizer, the cup member 63 may have its charging duct 72 with its outlet port 73 register with the port 74 (Figs. 5, 7) of the housing 75. The port 74 leads into the chamber 69 above the pans 71. As a vent to allow escape of air or vapor to permit charging of the closed chamber 69, the duct 76 from outside and through the member 63, extends to register with the port 77 communicating with the chamber 69 simultaneously with the registering of the ports 73, 74. With the vaporizer charged, a slight rotation of the member 63 closes the ports 74, 77, against escape of vapor from the vaporizer. The knurled headed member 63 carries the pointer 78 (Fig. 8) movable along the scale 79 to indicate filling position, and positions for full quantity of fluid to pass through the vaporizer chamber 69. With point 80 as the filling position, the graduations 81 indicate positions for allowing less than the full quantity of fluid to pass through the vaporizer, thereby permitting such enrichment of the fluid with the vapor as may be desired.

In the use of the rebreathing bag or reservoir, fluid exhaled by the patient coming back through the duct 67, with the sleeve 61′ disposed to place the port 62 open, the check valve 56 in the proportioning valve 48 cutting off backward flow, to the unmixed gases in the reservoirs 31, 32 this return fluid passes through the port 62 into the passages 82, 83, (Fig. 5) and into the chamber 84 having communication through the openings 85 with the flexible reservoir or rebreathing bag proper 86. Graduations 87 on the housing 75 for the vaporizer chamber 69 and chamber 84, are indications which may be followed in adjustment of the knurled ring 88 frictionally held by the packing 89 to vary the rebreathing capacity of the apparatus. This ring 88 carries the reservoir 86 on its connected bushing 90. Also connected to this bushing 90 of the ring 88, is the envelop or net 91, serving to maintain the rubber bag 86 in shape when under pressure and protect weak spots therein. The reservoir 86 being collapsible most readily, each inhalation of the patient primarily receives its supply from this rebreathing reservoir 86 until the suction on the delivery duct 60 overcomes the very slight pressure of the disk 56 and draws gas from the reservoirs 31, 32. Accordingly the withdrawal of gas from the bags 31, 32, is intermittent, being only as the disk 56 is raised by the inhalation of the patient, and even then the maximum flow is restricted by the adjusted position of the disk 56 the limit of movement of which away from the two apertures 55 in the top of the plug proportioning valve 48 may be limited or controlled by the adjustment of the threaded member of screw 57. The flapping of this disk 56 is in response to the breathing of the patient. Upon inhalation, after taking the supply from the rebreathing bag 86, the disk 56 is lifted from its seat on the two apertures 55 and in its bodily movement uniformly away therefrom upon the screw 57, the adjusted proportion of the equal pressure gases flows by way of duct 67 to the patient. Upon exhalation, either by its own weight or aided by the back pressure, the disk 56 seats at once and the bag 86 is filled, after which a further increase of pressure in the inhaler lifts the spring tensioned check valve 103 when the remainder of exhaled gases escape at this valve 103.

It is thus seen that as adjusted the net 91 is a means acted upon by the bag 86 to limit the inflations thereof. As this inflation occurs, or the draft from the mixing chamber 59 decreases, disk 56 as a control means governed by the inflations of the bag 86, renders the mixing valve mechanism inoperative in cutting off flow to the chamber 59, while on deflation of the bag 86, the lifting of this control means or disk 56 admits the two gases to the mixing chamber 59 for flow to the reservoir 86.

In the use of the respirator or gas administering apparatus the duct 67 may be connected to an inhaler or face nozzle 92 (Fig. 4) covering the nose and mouth, or a nasal nozzle 93 (Figs. 1, 2) may be used. In fact, the mechanism of the disclosure has a most wide range of utility. A field to which it is adapted with marked advantage is for analgesia, and anesthesia, say in dentistry, when a nasal nozzle is used to leave the mouth accessible, the patient breathing through the nose. The face mask (Figs. 4, 14) has relief valve 106 pivoted on stem 107 rotatably adjustable to increase the holding action toward closed position of spring 108.

The inhaler of nozzle 93 (Fig. 2) is shown as provided with the frame 94 having the bushing 95 therein carrying the loose disk 96 movable toward the flange 97 to close the opening through the bushing 95, and movable away from the flange 97 to open the ports 98 adjacent the lower or upset disk retaining portion of the bushing. This disk or washer 96 fits loosely in this cylindrical perforated portion of the bushing 95 and when resting against the flange 97 as forced thereagainst by air current, it is on its seat and closes this valve. This check valve acts in conjunction with the adjustable ports in the outer side of the bushing 95. The bushing 95 has the port 99 the opening of which is adjustable by rotating the cap 100 having a port movable thereby into and out of registry with the port 99. When the port in the cap 100 is adjusted out of registry with the port 99, the disk 96 is not moved by the breathing of the patient. The cap 100 may be held in adjusted position by the set screw 101.

The nozzle frame 94 is provided with an additional opening 102 normally closed by the disk 103 held in closed position by the spring 104. The action of this spring 104 may be varied by rotation of the hollow screw 105. A seating of disk 104 to close this valve is similar to disk 96 to close the ports in bushing 95.

The nozzle thus equipped permits, by adjustment of the port 99, a mixing of air with the fluid being administered, such mixing being susceptible of most delicate adjustment, thereby regulating the dilution with air of the other fluids delivered to the patient. This means of air dilution may be employed for diminishing the effects of the other fluids producing a state of analgesia, while by closing port 99 and preventing air dilution anesthesia may be produced when suitable proportions of the fluid are administered. This is a feature of great economy in manipulation of the apparatus. In exhaling, the used or lung exchanged volume of the gas is last to come, the upper passages expelling the inspiration in an unchanged state. Economy, especially in the administering of costly fluids, is obtained by allowing the early portion of the exhalation to pass back through the duct 67 to the rebreathing reservoir 86. Adjustment of the capacity of the reservoir 86 may be to the lung capacity or exhaling volume of the patient, particularly as to the unchanged gas volume. When the rebreathing reservoir is charged, the check member 56, shutting off further return through the delivery duct 60, pressure is established in the duct 67 to overcome the pressure against the check valve 104, and the used or changed portion of the exhalation may be allowed to escape. In the adjustments for the rebreathing reservoir, it is sometimes desirable to gather in this reservoir 86 some of the carbon dioxid or changed gases of the exhalation as a means for further modifying the intensity of the anesthetic or regulating the breathing of the patient or such other treatment as may be indicated by the condition of the patient. Rebreathing is not always practiced if the patient breathes normally and in such cases the valve 61′ closes the port 62.

The vaporizer, rebreathing reservoir, and nitrous oxid, may be cut out by the shifting of the handle 50 clockwise away from the arm 8 to have the pointer 51 toward the arm 7, and oxygen only supplied from said reservoir 31, or by turning horizontally outward the handle 22 of the emergency valve 21, the supply under pressure may be furnished direct. In cases of resuscitation, that is, to inflate the lungs with oxygen, restoring normal breathing, the vaporizer, rebreathing reservoir, and nitrous oxid is cut out when the valve handle 22 of emergency oxygen valve 21 on the left (Fig. 14) is turned as in Fig. 9, right hand side, delivering the oxygen above check 56 through passages 60, 67, and inhaler 92 or 93, into the lungs of the patient. The oxygen may be taken directly from the tank by opening valve 13 or preferably through valve 39, 40, by pressing the lever 34 against the bag to open port 45. In order to force the oxygen into the lungs passing any possible obstruction in the patient's air passages, the adjusting screw 105 is tightened on the nasal inhaler 93 or the exhalation valve 106 is held closed on the face inhaler 92 to prevent escape of oxygen while the lungs are inflated in imitation of inspiration. The inhaler is lifted at intervals to permit gases in the lungs to escape as in exhalation. This procedure is repeated until respirations are reestablished. This means of producing artificial respiration is of particular value in an apparatus used for anesthesia where oxygen put into the lungs at once readily saves life but if delayed a few moments may result in the immediate death of the patient.

The apparatus has great flexibility in its adaptations allowing the incorporation of the various elements to such degree as may be necessary, or the elimination for a short period, or entirely of various elements.

What is claimed and it is desired to secure by Letters Patent is:—

1. A respirator embodying two suspended supply reservoirs for fluid, and means for maintaining the contents of said reservoirs independent of each other and equalizing the fluid pressure in said reservoirs.

2. A respirator embodying two flexible fluid supply reservoirs, and means for equalizing the fluid pressure therein comprising a common extensible surrounding envelop for said reservoirs.

3. A respirator embodying suspended supply reservoirs for fluids, means for equalizing the pressure between said reservoirs and maintaining the contents separate, and a proportioning valve for controlling fluid flow from said reservoirs.

4. A respirator embodying suspended supply reservoirs for fluid, extensible reservoir enveloping means for equalizing fluid pressure between said reservoirs and maintaining the contents of said reservoirs separate, and a common proportioning valve for controlling fluid flow from said reservoirs.

5. A respirator embodying fluid supply ducts, an adjustable tapered stopper valve member for simultaneously controlling said ducts, said member having therein adjacent outlets for said ducts, and a check valve for said outlets.

6. A respirator embodying a first fluid supply reservoir, a second reservoir supplied from said first reservoir, automatic means exterior of the second reservoir actuable by the distention of the second reservoir for controlling the supply to said second reservoir, and a check valve between the second reservoir and the automatic means.

7. A respirator embodying a direct fluid supply reservoir including a bag, a reserve fluid supply reservoir for the bag, automatic means against which the bag engages for controlling supply from the reserve reservoir to the bag, and a check valve between the bag and the automatic means.

8. A respirator embodying a direct fluid supply flexible wall reservoir for fluid under pressure, a reserve fluid supply for fluid under greater pressure, automatic means exterior of the direct fluid supply reservoir actuable by the distention of the direct fluid supply reservoir for controlling the fluid to the direct supply reservoir from the reserve fluid supply, and a check valve between the flexible wall reservoir and the automatic means.

9. A respirator embodying a direct fluid supply reservoir including a collapsible bag, a reserve fluid supply reservoir, and pressure controlled means forced against said bag by pressure from said reserve reservoir to determine replenishing of said bag.

10. A respirator embodying a direct fluid supply reservoir comprising a bag having a collapsible envelop, a reserve fluid supply reservoir, and a valve having an arm engaging said envelop to maintain the valve closed against the pressure of the reserve fluid supply reservoir.

11. A respirator embodying a direct supply reservoir for fluid, a reserve supply duct to supply said reservoir, a delivery duct supplied by said reservoir, and an emergency connection for simultaneously disconnecting the reserve supply duct from the direct supply reservoir and connecting the delivery duct to the reserve supply duct independently of the direct supply reservoir, said connection comprising a three way valve.

12. A respirator embodying a direct fluid supply reservoir, a delivery duct connected thereto, a supply duct connected thereto, and a three way valve in the supply duct in communication with the delivery duct to disconnect the supply duct from the reservoir and directly connect the supply duct to the delivery duct independently of the reservoir.

13. A respirator embodying direct fluid supply reservoirs, a proportioning valve to which the reservoirs are connected, a reserve supply duct for one of said reservoirs, and emergency means for disconnecting the reservoir and connecting the reserve supply to said valve.

14. A respirator embodying a proportioning valve, ducts leading thereto, a direct fluid supply reservoir for one of said ducts, a reserve supply duct for said reservoir, and a cut-off device for disconnecting said reservoir and connecting said reserve supply duct to the proportioning valve direct.

15. A respirator provided with a delivery duct leading therefrom, a breathing nozzle to which said duct is connected, a rebreathing reservoir in said duct, and controllable means for by-passing the reservoir.

16. A respirator provided with a proportioning valve, a delivery duct leading therefrom, a breathing nozzle to which said duct extends, a rebreathing reservoir in said duct, and controllable means for by-passing the reservoir.

17. A respirator provided with a delivery duct leading therefrom, an adjustable rebreathing reservoir mounted on said duct, and controllable means for by-passing the reservoir.

18. A respirator provided with a delivery duct leading therefrom, a rebreathing reservoir mounted on said duct, and controllable means for by-passing the reservoir.

19. A respirator provided with a return check supply valve, a support therefor, a breathing nozzle, a delivery duct leading from said valve to said nozzle and having a section rigid with said support, a vaporizing device on said duct, a rebreathing reservoir device on said duct, one of said devices being carried by the rigid duct section, and means adjacent the vaporizer for disconnecting the vaporizer from the duct.

20. A respirator provided with a supply valve, a breathing nozzle, a delivery duct for the nozzle having a rigid section extending from the valve, support for the valve, a vaporizer and a rebreathing reservoir carried by said rigid duct section, and means adjacent the reservoir for disconnectng the reservoir.

21. A respirator provided with a supply valve, a breathing nozzle, a delivery duct from the valve to the nozzle, said duct having a rigid supporting section, a vaporizer carried by the rigid section, and a rebreathing reservoir carried by the vaporizer.

22. A respirator provided with a breathing nozzle, a delivery duct leading thereto, a controllable pressure gas supply reservoir for the duct, a support for the reservoir, a vaporizer connected to the duct in the extent of the duct from the reservoir toward the nozzle, and an adjustable rebreathing reservoir carried by the vaporizer and connected to the duct adjacent the supply reservoir and remote from the nozzle, said duct having a flexible section between the supply reservoir and the nozzle.

23. In an apparatus of the class described, the combination of a supporting post, a valve casing surmounting the post, and having gas inlet ports and an outlet port valve mechanism in said casing for governing the ports, a partition within said valve mechanism, a check valve resting on said partition, and a single manually operative means extending above the casing for operating the valve mechanism.

24. A respirator embodying a plurality of sources of fluid supply, suspended reservoirs supplied thereby, means for maintaining the contents of said reservoirs separate and the pressure of said contents equal, and valve mechanism common to said reservoirs for controlling fluid flow therefrom.

25. A respirator embodying suspended supply reservoirs for fluid, means for equalizing the pressure between said reservoirs and maintaining the contents separate, and proportioning valve mechanism for controlling fluid flow from said reservoirs.

26. In an anesthetic apparatus arranged to be equipped with a compressed gas supply passage, a regulating valve therefor, an expansible gas bag, bag expansion governed means for controlling said valve, said means including a diaphragm isolating the valve, and bag actuated means exterior of the diaphragm for operating the valve through the diaphragm.

27. In an apparatus of the class described, the combination of a supporting post, a duct providing head surmounting said post and having two gas inlets and a gas outlet, said head including two pairs of arms, one pair disposed at right angles to the other pair, an extensible reservoir carried by said head, a hollow plug valve for controlling gas flow from the reservoir, and a check valve carried by said plug valve.

28. In an apparatus of the class described, the combination of a head, a bag connected to said head, a hollow plug valve for controlling gas flow from the bag, and a check valve carried by said plug valve.

29. A gas administering device having a chamber, two supply means for gases to said chamber, each including a reserve supply duct, and a direct supply reservoir, port means fixing the proportion between the gases supplied to said chamber from said reservoirs, valves exterior of the reservoirs controlling gas flow from the reserve supply ducts to the direct supply reservoirs, and reservoir pressure control means for adjusting the valves to control the flow to the direct supply reservoirs while the port means maintains said fixed proportion.

30. A gas administering device having a chamber, two gas supply ducts to said chamber, a direct supply reservoir for each duct, pressure regulating means exterior of said reservoirs for controlling gas flow thereto, and flow controlling proportioning means for determining a fixed proportion between said supplies of gas delivery to said chamber and flow checking means in the chamber movable to intercept gas flow thereinto, said flow checking means being movable relatively to said flow controlling proportioning means.

31. A gas administering device comprising a source of nitrous oxid under pressure, a source of oxygen under pressure, a chamber, ducts for conducting said gases independently from said sources to the chamber including flow controlling proportioning means for determining a fixed proportion of gas delivery from said sources to said chamber, control means in said ducts for separately regulating the delivery pressures of the respective gases for flow to said chamber, and means for determining the equalization of the delivery pressures of said gases.

32. A gas administering device comprising a support, a first bag carried by said support, a duct arm extending from said support, a second bag on said duct arm connected by the duct of the arm to the first bag, and manually controllable means for rendering the second bag a rebreathing bag by opening a passage to the second bag from the duct and leaving the duct passage open past the second bag.

33. A gas administering machine comprising a plurality of sources of fluid supply under pressure, a mixing chamber, a passage way leading from each of said sources of supply to the mixing chamber for conducting each of said gases separately into the mixing chamber, a valve in each of said passageways for admitting gas from its respective source thereinto, two flexible expansion members each having separate connection with one of said passage ways and constituting a reservoir for a relatively large volume of gas at a relatively low pressure for delivery therefrom through said passage way to the mixing chamber, and means caused to operate by the movement in expansion and contraction of said flexible members for opening and closing said valves to admit and shut off flow of gas into said reservoirs.

34. A gas administering machine comprising a source of oxygen supply and a source of nitrous oxid supply each under pressure, a mixing chamber, a passageway leading from said oxygen supply and a separate passage way leading from said nitrous oxid supply to the mixing chamber for conducting each of said gases separately into the mixing chamber, valve mechanism at the entrance to the mixing chamber for regulating the amount of oxygen and the amount of nitrous oxid entering said mixing chamber from the respective passage ways so as to produce a mixture thereof in predetermined proportions, a valve in each of said passage ways for admitting oxygen and nitrous oxid respectively into its passage way, a flexible expansion member having connection with the oxygen passageway, and a flexible expansion member having connection with the nitrous oxid passage way, each of said members constituting a reservoir for a relatively large volume of gas at a relatively low pressure for delivery therefrom through its passage way to the mixing chamber, and means caused to operate by the movement in expansion and contraction of said flexible members for opening and closing said valves to admit and shut off the flow of gas into said reservoirs.

35. A gas administering machine comprising a plurality of gas supplies each separately connected to a supply line, an expansion chamber in each of said connections, valves in each of said connections, a flexible expansion member in each of said connections adapted to be inflated and deflated by the introduction and withdrawal of gas therefrom, and means operative from said expansion members for operating said valves to cause them to admit and cut off delivery of gas to the expansion members.

36. A gas administering machine comprising an oxygen container and a nitrous oxid container, valves for each of said containers, expansible gas reservoirs each having connection with one of said valves, and means operative from the expansion of said reservoirs for operating said valves to cause them to deliver a variable flow of oxygen and nitrous oxid to the respective reservoirs, and means controlling the delivery of said gases at reduced pressure and in a constant proportion from said reservoirs.

37. In a device of the class described, a series of fluid containers, valve and flexible expansion chambers having connection with said containers, means operative from the expansion of said chambers for operating said valves to provide a mixture of the gases, means controlling the flow of the respective gases to vary the proportion thereof, and an indicator for indicating the proportion.

38. A gas administering machine comprising a compressed gas cylinder, a regulating valve in communication with the gas supply from such cylinder, an expansible elastic gas bag constituting a reservoir for a relatively large volume of gas at a relatively low pressure, a gas administering passage having communication with said reservoir, means governed by the inflation and deflation of the reservoir for controlling the regulating valve to admit or cut off gas from the said reservoir, and means for varying the pressure imposed upon the gas by and in said reservoir.

39. A gas administering machine comprising a pair of compressed gas cylinders, one containing xoygen and the other nitrous oxid, a regulating valve in communication with the gas supply from each cylinder, an expansible elastic gas bag having connection with each cylinder and constituting a reservoir for a relatively large volume of gas at a relatively low pressure, a gas administering passage having separate communication with each reservoir, separate means governed by inflation and deflation of each reservoir for controlling the respective regulating valves to admit or cut off gas from said reservoirs, and means for varying the pressure imposed upon the gas by and in each reservoir.

40. A gas administering machine comprising a plurality of gas supplies each separately connected to a mixing chamber and patient's supply line, valves in each of said connections, a flexible expansion member in each of said connections adapted to be inflated and deflated by the introduction and withdrawal of gas therefrom, and means connected with each of said valves and caused to operate by reason of movements of the walls of one of said expansion members for operating said valves to cause them to admit and cut off delivery of gas to the respective expansion members.

41. An anaesthetizing apparatus having a mixing chamber, means for supplying thereto from independent sources of supply a plurality of gases under pressure, an inhaler, a gas-bag adapted to communicate with and be shut off from said inhaler and said mixing chamber, and a single shiftable valve whereby the mixed gases may be delivered to said inhaler alone or to both said inhaler and said gas-bag.

42. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, each of said valves including a housing providing a guide, there being a port in each of said housings, and a member in each of said housings shiftable along said guides for opening and closing said ports, and reservoir pressure control means for adjusting the valves by affecting shifting of said members in said housings as to said ports in thus adjusting the valves to control the flow of the respective gases to the direct supply reservoirs for flow from thence by way of said port means to said chamber.

43. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, reservoir pressure control means for adjusting the valves to control the flow to the direct supply reservoirs, a delivery duct for the mixed gases as thus maintained for supply to said chamber, and an inhaler mounted on said delivery duct.

44. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, reservoir pressure control means for adjusting the valves to control the flow to the direct supply reservoirs, a delivery duct for the mixed gases as thus maintained for supply through said port means to said chamber, an inhaler mounted on said delivery duct, and a bag in communication with said inhaler through said delivery duct.

45. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, reservoir pressure control means for adjusting the valves to control the flow to the direct supply reservoirs, a delivery duct for the mixed gases as thus maintained for supply through said port means to said chamber, an inhaler mounted on said delivery duct, a bag in communication with said delivery duct, and means for varying the capacity of said bag, whereby said bag is an adjustable volume receiver affecting by said adjustments changes in the flow volumes of the gases from the direct supply reservoirs through said port means to said chamber in the regular operation of the device.

46. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, reservoir pressure control means for adjusting the valves to control the flow to the direct supply reservoirs, a delivery duct for the mixed gases as thus maintained for supply to said chamber, an inhaler mounted on said delivery duct, and an exhaling valve on said inhaler adjustable to vary the proportion of exhaled gas passing from said inhaler to said duct for thereby varying the total volume of flow of gases through said port means.

47. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, reservoir pressure control means for adjusting the valves to control the flow to the direct supply reservoirs, a delivery duct for the mixed gases as thus maintained for supply through said port means to said chamber, an inhaler mounted on said delivery duct, a bag in communication with said inhaler through said delivery duct, and an exhaling valve for spilling exhaled gas as the bag is inflated.

48. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow from the reserve supply ducts to the direct supply reservoirs, reservoir pressure control means for adjusting the valves to control the flow to the direct supply reservoirs, a delivery duct for the mixed gases as thus maintained for supply to said chamber, an inhaler mounted on said delivery duct, and an inlet valve adjustable to permit mixture of outside air with said gases from the port means whereby the volume of gases passing said port means is thereby changed.

49. A gas administering device having a chamber, two supply means for gases to said chamber, each including a reserve supply duct and a direct supply reservoir, port means fixing the proportion between the gases supplied to said chamber from said reservoirs, valves exterior of the reservoirs controlling gas flow to the direct supply reservoirs, a delivery duct for the mixed gases as thus maintained for supply to said chamber, an inhaler connected to said delivery duct, and an exhaling valve embodying a port, there being threaded means adjacent said port, a disk for closing said port, a spring, and a rotary threaded member coacting with the threaded means as an exhaling valve adjusting device to vary the action of the spring and thereby increase or decrease the volume of exhaled gas passing from said exhaling valve for thereby varying the total volume of flow of gases through said port means.

In witness whereof, I affix my signature.

ELMER I. McKESSON.